(12) United States Patent
Climent-Johansson et al.

(10) Patent No.: US 6,472,515 B1
(45) Date of Patent: Oct. 29, 2002

(54) RESPONSE ELEMENT

(75) Inventors: Isabel Climent-Johansson, Stockholm; Karin Dahlman-Wright, Bromma; Staffan Lake, Lidingö ; Wyeth Wasserman, Stockholm, all of (SE)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 09/645,629

(22) Filed: Aug. 24, 2000

Related U.S. Application Data

(60) Provisional application No. 60/151,867, filed on Aug. 31, 1999.

(30) Foreign Application Priority Data

Aug. 26, 1999 (SE) ................................. 9903009
Nov. 25, 1999 (SE) ................................. 9904269

(51) Int. Cl.$^7$ ........................ C07H 21/04; C12N 5/02; C12N 5/00
(52) U.S. Cl. ..................... 536/23.1; 435/325; 435/375
(58) Field of Search .................. 536/23.1; 435/325, 435/375, 6, 7.1

(56) References Cited

PUBLICATIONS

Pierrou et al. Cloning and characterization of seven human forkhead proteins: binding site specificity DNA bending EMBO journal vol. 13 no. 20 pp. 5002–5012 1994.*
Pierrou et al. Cloning and characterization of seven human forkhead proteins: binding site specificity and DNA bending L20 Answer 7 of 7 registry copyright 2001 seq. aacatgttc.*
Kaufmann et al, *Mechanisms of Development*, 57:3–20 (1996).
Suwanickul et al, *Journal of Biological Chemistry*, 268(23):17063–17068 (1993).
Allander et al, *Endocrinology*, 138(10):4291–4300 (1997).
DeFronzo, *Diabetes Reviews*, 5:177–269 (1997).
O'Brien et al, *Diabetes Mellitus*, Lippincott–Raven Publishers, Philadelphia, pp. 234–242 (1996).
Kops et al, *Nature*, 398:630–634 (1999).
Guo et al, *J. Biol. Chem.*, 274:17184–17192 (1999).
Ayala et al, *Diabetes*, 48:1885–1889 (1999).
Durham et al, *Endocrinology*, 140:3140–3146 (1999).
Coffer et al. *Biochem. J.*, 335:1–13 (1998).
Paradis, *Genes & Development*, 12:2488–2498 (1998).
Kahn, *Cell*, 92:593–596 (1998).
Ogg et al, *Nature*, 389:994–999 (1997).
Lin et al, *Science*, 278:1319–1322 (1997).
Anderson et al, *Genomics*, 47:187–199 (1998).
Bennicelli et al, *Oncogene*, 14:195–202 (1995).
Borkhardt et al, *Oncogene*, 14:195–202 (1997).
Fredericks et al *Molecular and Cellular Biology*, 15:1522–1535 (1995).
James et al, *Recent Res. Devel. Biochem.*, 1:63–76 (1999).
Brunet et al, *Cell*, 96:857–868 (1999).

* cited by examiner

*Primary Examiner*—Remy Yucel
*Assistant Examiner*—Konstantina Katcheves
(74) *Attorney, Agent, or Firm*—Fish & Richardson P.C.

(57) ABSTRACT

The present invention is directed to a novel Afx response element comprising the nucleotide sequence AACATGTT, said nucleotide sequence having a DNA binding site for the human fork head transkription factor Afx. The invention also relates to the use of the Afx response element in the screening for genes as diabetes drug targets and in the bioinformatic analysis of the human genome, said genes in turn being useful in other screening methods for compounds modifying the insulin receptor signaling pathway. A further aspect of the invention is a vector construct comprising the novel nucleotide sequence, a host cell transformed with said vector construct as well as the fusion protein expressed by said host cell.

15 Claims, 8 Drawing Sheets

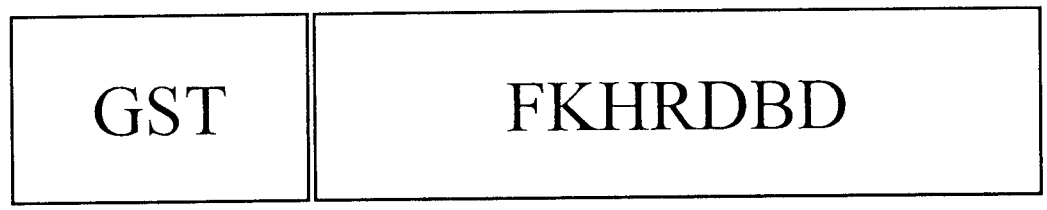
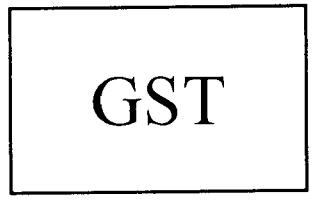
Figure 1

Binding selection with GST-AfxDBD

```
---GCCCCACTCCATAACATGTTGTTC-------
---GCCCGCGGATAACAACATGTTGTTG-------
---GGCCGAC--TATCAACATGTTTGCCTG-----
GNAACCGNCTGTTGTNAACATGTTG---------
GGACGGTAGGGAGTAAACATGTTG---------
---GGCGGGACGTGTCAACATGTTGTGC-------
---GGCACCCGCAGTAAACATGTTATGC-------
GGCATAGCTCTGTGTAAACATGTTG---------
GGCAGGACGGTACACAAACATGTTG---------
---------GGCATCAACATGTTTATAATGGGTG
-------GGCAGCGGTAAACATGTTGTCTCC----
-----GGCCCACGGTCAACATGTTTTGATG-----
GGCGGGACTCGGGTAAACATGTTG---------
--------GGAGCATAAACATGTTGTTGGCGGC--
---------GCGGTAAACATGTTGNGATCAGNG-
------GGGCGGGATAAACATGTTATGCTCC----
----GGTAGGCAGCACAACATGTTTACCC------
---GGTACATACGCTAAACATGTTGTGC-------
-----GGGAGCCCCATAACATGTTTTCACG-----
---GCGCCCAGGCATAAACATGTTGTTG-------
      G    G   GTAAACATGTTGT
```

Figure 3

AFX FREQUENCY MATRIX

| Pos | 1 | 2 | 3 | 4 | 5 | 6 | 7 | 8 | 9 | 10 | 11 | 12 |
|---|---|---|---|---|---|---|---|---|---|---|---|---|
| A | 16.5 | 0.0 | 24.3 | 24.0 | 0.0 | 25.0 | 0.0 | 0.0 | 0.0 | 0.0 | 1.2 | 17.0 |
| C | 2.5 | 20.0 | 0.2 | 0.0 | 23.0 | 0.0 | 0.0 | 0.0 | 0.0 | 0.0 | 0.2 | 0.0 |
| G | 1.5 | 0.0 | 0.2 | 1.0 | 0.0 | 0.0 | 0.0 | 1.0 | 0.0 | 1.0 | 2.2 | 3.0 |
| T | 4.5 | 5.0 | 0.2 | 0.0 | 2.0 | 0.0 | 25.0 | 0.0 | 24.0 | 24.0 | 21.3 | 5.0 |

AFX WEIGHT MATRIX
(with Knowledge Adaptation)

| Pos | 1 | 2 | 3 | 4 | 5 | 6 | 7 | 8 | 9 | 10 | 11 | 12 |
|---|---|---|---|---|---|---|---|---|---|---|---|---|
| A | 1.24 | -2.58 | 1.77 | 1.75 | -2.58 | 1.81 | -9.99 | -9.99 | -2.58 | -2.58 | -1.61 | 1.28 |
| C | -1.00 | 1.50 | -2.37 | -2.58 | 1.69 | -9.99 | -9.99 | -9.99 | -1.74 | -2.58 | -2.37 | -2.58 |
| G | -1.45 | -2.58 | -2.37 | -1.74 | -2.58 | -9.99 | -9.99 | 1.81 | -2.58 | -1.74 | -1.12 | -0.82 |
| T | -0.38 | -0.26 | -2.37 | -2.58 | -1.21 | -9.99 | 1.81 | -9.99 | 1.75 | 1.75 | 1.59 | -0.26 |

Figure 5

```
ATGTCCCCTATACTAGGTTATTGGAAAATTAAGGGCCTTGTGCAACCCAC
TCGACTTCTTTTGGAATATCTTGAAGAAAAATATGAAGAGCATTTGTATG
AGCGCGATGAAGGTGATAAATGGCGAAACAAAAAGTTTGAATTGGGTTTG
GAGTTTCCCAATCTTCCTTATTATATTGATGGTGATGTTAAATTAACACA
GTCTATGGCCATCATACGTTATATAGCTGACAAGCACAACATGTTGGGTG
GTTGTCCAAAAGAGCGTGCAGAGATTTCAATGCTTGAAGGAGCGGTTTTG
GATATTAGATACGGTGTTTCGAGAATTGCATATAGTAAAGACTTTGAAAC
TCTCAAAGTTGATTTTCTTAGCAAGCTACCTGAAATGCTGAAAATGTTCG
AAGATCGTTTATGTCATAAAACATATTTAAATGGTGATCATGTAACCCAT
CCTGACTTCATGTTGTATGACGCTCTTGATGTTGTTTTATACATGGACCC
AATGTGCCTGGATGCGTTCCCAAAATTAGTTTGTTTTAAAAAACGTATTG
AAGCTATCCCACAAATTGATAAGTACTTGAAATCCAGCAAGTATATAGCA
TGGCCTTTGCAGGGCTGGCAAGCCACGTTTGGTGGTGGCGACCATCCTCC
AAAATCGGATCTGGTTCCGCGTGGATCTGGTACCGAGCTCGGATCCGGGG
CTGTAACAGGTCCTCGGAAGGGAGGCTCCCGCCGGAATGCCTGGGGAAAT
CAGTCATATGCAGAACTCATCAGCCAGGCCATTGAAAGCGCCCCGGAGAA
GCGACTGACACTTGCCCAGATCTACGAGTGGATGGTCCGTACTGTACCCT
ACTTCAAGGACAAGGGTGACAGCAACAGCTCAGCAGGATGGAAGAACTC
GATCCGCCACAACCTGTCCTGCACAGCAAGTTCATCAAGGTTCACAACG
AGGCCACCGGCAAAGCTCTTGGTGGATGCTGAACCCTGAGGGAGGCAA
GAGCGGCAAAGCCCCCGCCGCCGGGCCGCCTCCATGGATAGCAGCAGA
AGCTGCTCCGGGGCCGCAGTAAAGCC
```

Figure 7

MSPILGYWKIKGLVQPTRLLLEYLEEKYEEHLYERDEGDKWRNKKFELGL
EFPNLPYYIDGDVKLTQSMAIIRYIADKHNMLGGCPKERAEISMLEGAVL
DIRYGVSRIAYSKDFETLKVDFLSKLPEMLKMFEDRLCHKTYLNGDHVTH
PDFMLYDALDVVLYMDPMCLDAFPKLVCFKKRIEAIPQIDKYLKSSKYIA
WPLQGWQATFGGGDHPPKSDLVPRGSGTELGSGAVTGPRKGGSRRNAWGN
QSYAELISQAIESAPEKRLTLAQIYEWMVRTVPYFKDKGDSNSSAGWKNS
IRHNLSLHSKFIKVHNEATGKSSWWMLNPEGGKSGKAPRRRAASMDSSSK
LLRGRSKA

Figure 8

RESPONSE ELEMENT

CROSS REFERENCE TO RELATED APPLICATIONS

This application claims priority from Swedish Patent Application No. 9903009-0, filed Aug. 26, 1999, Swedish Patent Application No. 9904269-9, filed Nov. 25, 1999, and U.S. Provisional Patent Application Serial No. 60/151,867, filed Aug. 31, 1999. These applications are incorporated herein by reference in their entirety.

TECHNICAL FIELD

The present invention is directed to a novel Afx response element comprising a DNA binding site for the human fork head transcription factor Afx, as well as to its use in the screening for genes.

BACKGROUND AND PRIOR ART

Diabetes and obesity are global health problems. Diabetes is the leading cause of blindness, renal failure, and lower limb amputations in adults, as well as the major risk factor for cardiovascular disease and stroke. Normal glucose homeostasis requires the finely tuned orchestration of insulin secretion by pancreatic beta-cells in response to subtle changes in blood glucose levels, delicately balanced with secretion of counter-regulatory hormones such as glucagon.

Type 1 diabetes or insulin-dependent diabetes mellitus, IDDM, results from autoimmune destruction of pancreatic beta-cells causing insulin deficiency. Type 2 or NIDDM (non-insulin dependent diabetes mellitus) is characterized by a triad of (1) resistance to insulin action on glucose uptake in peripheral tissues, especially skeletal muscle and adipocytes, (2) impaired insulin action to inhibit hepatic glucose production, and (3) dysregulated insulin secretion (R. A. DeFronzo, (1997); *Diabetes Reviews*, 5, pp. 177–269). After glucose infusion or ingestion (i.e., in the insulin stimulated state), the liver in type 2 diabetic patients overproduces glucose and the muscle glucose uptake is decreased leading to both hyperinsulinemia and hyperglycemia.

Insulin regulates a wide range of biological processes, including glucose transport, glycogen synthesis, protein synthesis, cell growth, and gene expression. Insulin regulates these processes by altering the concentration of critical proteins or by producing activity-altering modifications of pre-existing enzyme molecules. It is clear that insulin can have both positive and negative effects on the transcription of specific genes (R. M. O'Brien, et al. (1996). *Gene regulation in Diabetes Mellitus* Lippincott-Raven publishers, Philadelphia. pp. 234–242). The genes regulated by insulin encode proteins that have well-established metabolic connection to insulin, but also secretory proteins/hormones, integral membrane proteins, oncogenes, transcription factors, and structural proteins. Not unexpectedly, this type of regulation of gene expression is seen in the primary tissues associated with the metabolic actions of insulin, namely, liver, muscle, and adipose tissue, but also in tissues not commonly associated with these metabolic effects.

The cis/trans model of trancriptional control can be utilized to understand how insulin regulates gene transcription at the molecular level. The fidelity and frequency of initiation of transcription of eukaryotic genes is determined by the interaction of cis-acting DNA elements with trans-acting factors. The specific sequence of the cis-acting element determines which trans-acting factor will bind. Several cis-acting elements thai mediate the effect of insulin on gene transcription have recently been defined. These are referred to as insulin response sequences or elements (IRSs/IREs) (R. M. O'Brien, et al. (1996). *Gene regulation in Diabetes Mellitus* Lippincott-Raven publishers, Philadelphia. pp. 234–242; G. J. P Kops, et al. (1999). *Nature*, 398, pp. 630–634; S. Guo et al (1999). *J.Biol.Chem.* 274, 17184–17192; J. E. Ayala et al. (1999). *Diabetes*, 48, 1885–1889; and S. K. Durham et al. (1999). *Endocrinology*, 140, 3140–3146). However, it should be mentioned that to date, there is lack of agreement upon a single insulin response element. Also, that formation of heterodimers between two trans-acting factors can alter their ability to activate transcription, their affinity for DNA or sequence specificity.

One important question in the study of insulin-regulated gene transcription is how a signal passes from the insulin receptor in the plasma membrane through the cytoplasm and the nuclear membrane to a specific trans-acting factor binding to an IRE. Well-characterised signal transduction mechanisms downstream of the insulin receptor involve cascades of kinase/phosphatase reactions, including, among others, the phosphatidylinositol 3-kinase (PI3K) pathway (P. J. Coffer, et al. (1998), *Biochem. J*. 335, pp. 1–13; S. Paradis, et al. (1998); *Genes & Development*, 12, pp. 2488–2498; B. B. Kahn (1998); *Cell*, 92, pp. 593–596). Binding of insulin to its cell surface transmembrane receptor stimulates receptor autophosphorylation and activation of the intrinsic tyrosine kinase activity, which results in phosphorylation of several cytosolic docking proteins called insulin receptor substrates (IRSs). IRSs bind to various effector molecules including the 85 kDa regulatory subunit of P13K. This localizes the 110 kDa catalytic domain of P13K to the plasma membrane. The activated P13K phosphorylates membrane bound phosphoinositides (PtdIns), generating PtdIns(3,4)P2 and PtdIns(3,4,5)P3. These lipids bind to the pleckstrin homology (PH) domain of protein kinase B (PKB, also known as Akt) leading to its accumulation at the cell membrane. The binding causes a conformational change in PKB that makes it more accessible to phosphorylation, which is necessary for its activation. The kinases, which phosphorylate PKB, are themselves targets for lipid products of P13K and are therefore also localized to the membrane. These kinases are called phosphoinositide-dependent protein kinases (PDK1 and PDK2). Activated PKB dissociates from the membrane and moves to the nucleus and other subcellular compartments.

The Insulin-like Pathway in the Nematode *Caenorhabditis elegans*

Recent studies in the nematode *Caenorhabditis elegans* show that a major target of the Akt/PKB homologues, akt-1 and akt-2, is a transcription factor (S. Paradis, et al. (1998); *Genes & Development*, 12, pp. 2488–2498). An insulin receptor-like signaling pathway regulates *C. elegans* metabolism, development, and longevity. This pathway is required for reproductive growth and normal metabolism. Mutations in the insulin receptor homologue daf-2 or in the P13K homologue age-1 cause animals to arrest as dauers, shift metabolism to fat storage, and live longer. This regulation of *C. elegans* metabolism is similar to the physiological role of mammalian insulin in metabolic regulation. Mutations in the gene daf-16, which encodes a fork head transcription factor that acts downstream of the kinases, suppress the effects of mutations in daf-2 or age-1 (S. Ogg et al. (1997); *Nature*, 389, pp. 994–999; K. Lin et al. (1997); *Science*, 278, pp. 1319–1322). The principal role of DAF- 2/AGE-1 signaling is thus to antagonize DAF-16. Paradis et al. showed further that inactivation of C. elegans Akt/PKB signaling also causes a dauer constitutive phenotype, and that loss-of-function mutations in the Fork head transcription factor DAF-16 relieves the requirement for Akt/PKB signaling to repress dauer formation. This indicates that DAF-16 is a negatively regulated downstream target of Akt/PKB signaling. DAF-16 contains four consensus sites for Akt/PKB phosphorylation, which indicate that the kinase exert the negative regulatory effect by directly phosphorylating DAF-16 and altering its transcriptional regulatory function.

Human DAF-16 Homologues

The most closely related proteins, identified so far, to DAF-16 are the human fork head transcription factors Afx, FKHR and FKHRL1. Based on amino acid sequence comparison of their fork head DNA-binding domains, Afx, FKHR, and FKHRL1 share about 60–65% identity with DAF-16 (S. Ogg et al. (1997); Nature, 389, pp. 994–999). Afx shares 83% and 81% identity to the fork head domains of FKHR and FKHRL1, respectively (M. J. Anderson et al. (1998); Genomics, 47, pp.187–199). Although this high homology is confined to the fork head domain, amino acid sequences on either side of this domain show little relatedness. However, there are several amino acid stretches outside the fork head domain that show marked sequence conservation. A N-terminal region of 24 amino acids is 75–83% conserved, and the C-terminal ends of each protein where the transactivation domains are located (J. L. Bennicelli et al. (1995). Oncogene, 11, pp. 119–130 and G. J. P. Kops, et al. (1999). Nature, 398, pp. 630–634 ) contain several stretches of homology. The genes for the human DAF-16 homologues were first identified at chromosomal breakpoints in human tumours (A. Borkhardt et al. (1997); Oncogene, 14, pp. 195–202; W. J Fredericks, et al. (1995); Molecular and Cellular Biology, 15, pp. $15^22$–1535; M. J. Anderson et al. (1998); Genomics, 47, pp.187–199). These tumours were associated with translocation-generated fusion proteins, Afx/mixed-lineage leukemia (MLL) fusion protein in acute leukemias, and PAX3/FKHR fusion protein in alveolar rhabdomyosarcomas. These fork head proteins contain three PKB phosphorylation sites. It has recently been proposed that Afx is a substrate for PKB (S. R. James et al. Recent Res. Devel. Biochem., 1 (1999), pp. 63–76; and G. J. P Kops, et al. (1999); Nature, 398; pp. 630–634). The phosphorylation of Afx increases after insulin stimulation, and this in terms reduces the activity of the transcription factor. Thus, Afx is negatively regulated by PKB.

A. Brunet, et al. demonstrated in Cell 96 (1999); pp. 857–868, that PKB also regulates the activity of FKHRL1. In the presence of survival factors, such as insulin-like growth factor 1 (IGF1) and neurotrophins, PKB phosphorylates FKHRL1, leading to FKHRL1's retention in the cytoplasm. Survival factor withdrawal leads to FKHRL1 dephosphorylation, nuclear translocation, and target gene activation.

It has been shown that Afx can activate insulin response element-driven reporter genes (S. R. James et al. Recent Res. Devel. Biochem., 1 (1999), pp. 63–76; and G. J. P Kops, et al. (1999); Nature, 398; pp. 630–634). However, it has not been shown if these are the optimal response elements, if Afx, FKHR, and FKHRL1 show identical or similar DNA-binding characteristics, or how specific they are with regard to DNA binding.

Given a representative sampling of DNA sequences to which a transcription factor will bind, it is possible to generate a specific profile or model which can be applied to identify DNA sequences to which a transcription factor will bind in vitro. Such a model is useful for the identification of genes with a potential binding site for the transcription factor in the promoter, intergenic sequences, or 3' regions (the introns and sequences which flank the first and last exons). Subset of the found genes can be created, e.g. based on biological knowledge.

THE INVENTION

The object of the present invention was to find a response element comprising a DNA binding site for the human fork head transcription factor Afx. In accordance with the present invention, a novel Afx response element comprising the nucleotide sequence AACATGTT is hereby provided, said nucleotide sequence having a binding site for the human fork head transkription factor Afx.

The DNA binding specificity of the fork head protein Afx has in accordance with the present invention been identified. The binding site for Afx is a palindromic sequence, AACATGTT.

The present invention provides the basis for future computer analysis for the identification of genes that are potentially regulated by the transcription factor Afx. The use of this found response element is thus useful in the screening for genes that may be used as diabetes drug targets, as well as in bioinformatic analysis of the human genome. Thus, the present invention provides a subset of genes transcriptionally responsive to insulin, said transcription responsive element being useful in the construction and development of assays which enable and facilitates the analysis of genes interacting with the cytokine receptor signaling pathways (e.g. the insulin receptor). Genes found in such screening may in turn be useful in additional screening methods for compounds modifying the insulin receptor signaling pathway.

BRIEF DESCRIPTION OF THE DRAWINGS

FIG. 1 is a schematic presentation of the fusion proteins used in the selection procedure.

FIG. 3 is an alignment of the 20 sequences (SEQ ID NOs: 1–20, respectively) selected for GST/AfxDBD. Each sequence contains 25 nucleotides and at the bottom is shown in bold and italics the conserved core motif and partially conserved flanking nucleotides, respectively (SEQ ID NO:21).

FIG. 5 shows the AfX frequency and weight matrix.

FIG. 7 shows the nucleotide sequence encoding GST-AfxDBD (SEQ ID NO:22).

FIG. 8 is the corresponding amino acid sequence for the protein expressed by GST-AfxDBD (SEQ ID NO:23).

DEFINITIONS AND ABBREVIATIONS

Figure 2:
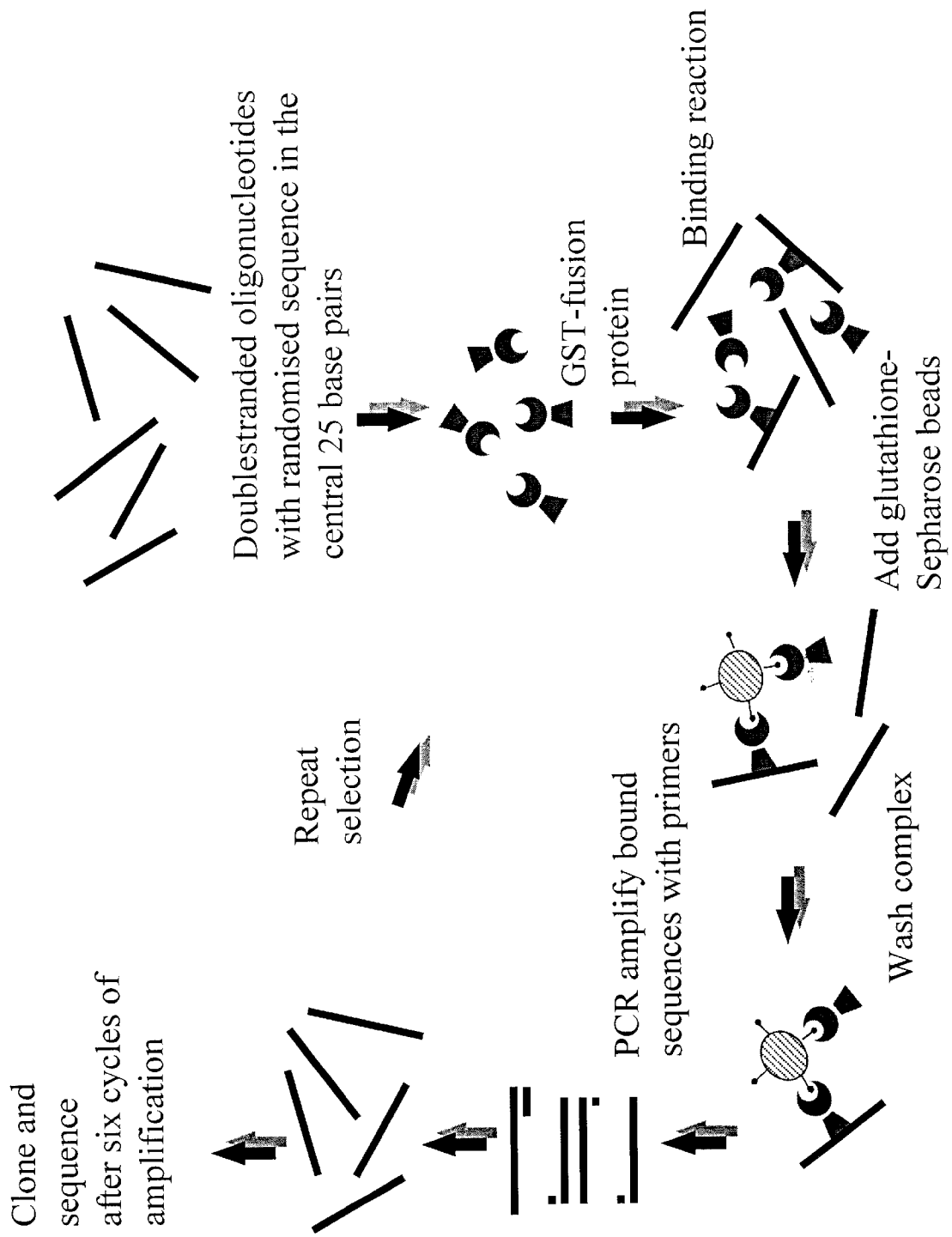
FIG. 2 is a schematic presentation of the selection and amplification cycle procedure to isolate high-affinity DNA binding sites for the transcription factors.

In order to provide a clear and consistent understanding of the invention, the following definitions are provided.

BSA: Bovine Serum Albumin

C-terminal: Carboxy-terminal dNTP: Deoxy Nucleotide Triphosphate

DTT: Dithiothreitol

EDTA: Ethylenediaminetetraacetic acid

GST: Glutathione S-Transferase

HEPES: N-[2-hydroxyethyl]piperazine-N'-[2-ethanesulfonic acid]

IPTG: Isopropylthiogalactoside, an inducer for the E.Coli lac operon

MOPS buffer: 3-[N-Morpholino]propanesulfonic acid

NuPAGE®, from the company Novex/Invitrogen

PBS: Phosphate buffered saline

PCR: Polymerase Chain Reaction

PMSF: Phenylmethylsulfonyl fluoride

SDS-PAGE: Sodium dodecyl sulfate polyacrylamide gel electrophoresis

Tris-HCl: Tris(hydroxymethyl)aminomethane

Triton X-100: t-octylphenoxypolyethoxyethanol

Tween 20: Polyoxyethylene sorbitan monolaurate

X-gal: X-galactose

Plasmid: A cloning vector which is able to replicate autonomously in a host cell, and which is characterized by one or a small number of restriction endonuclease recognition sites. A foreign DNA fragment may be spliced into the plasmid/cloning vector at these sites in order to bring about the replication and cloning of the fragment. The vector may contain a marker suitable for use in the identification of transformed cells. For example, markers may provide tetracycline resistance or ampicillin resistance.

Expression: Expression is the process by which a polypeptide is produced from DNA. The expression process involves the transcription of the gene into mRNA, and the translation of this mRNA into a polypeptide.

Expression vector: A vector similar to a cloning vector but which is capable of inducing the expression of the DNA that has been cloned into it, after transformation into a host. The cloned DNA is usually placed under the control of (i.e. operably linked to) certain regulatory sequences such as promoters or enhancers. Promoter sequences may be constitutive, inducible or repressible.

Host: Any prokaryotic or eukaryotic cell that is the recipient of a replicable expression vector or cloning vector, is the "host" for that vector. The term encompasses prokaryotic or eukaryotic cells that have been engineered to incorporate a desired gene on its chromosome or in its genome. Examples of cells that can serve as hosts are well known in the art, as are techniques for cellular transformation (see e.g. Sambrook et al. *Molecular Cloning: A Laboratory Manual*, 2$^{nd}$ ed. Cold Spring Harbor (1989)).

Promoter: A DNA sequence typically found in the 5' region of a gene, located proximal to the start codon. Transcription is initiated at the promoter. If the promoter is of the inducible type, then the rate of transcription increases in response to an inducing agent.

Response element: The nucleotide sequence of a cis-acting element located in the promotor region of a gene and involved in transcriptional control. A response element is a short DNA sequence located in the promoter, intergenic sequences, or 3' regions (the introns, and sequences which flank the first or last exons) of a gene and that is involved in transcriptional control.

Scoring: For any given sequence as wide as the model, take the corresponding numbers for the observed nucleotide at each position and sum the numbers.

I. Construction of Plasmids

Figure 6:
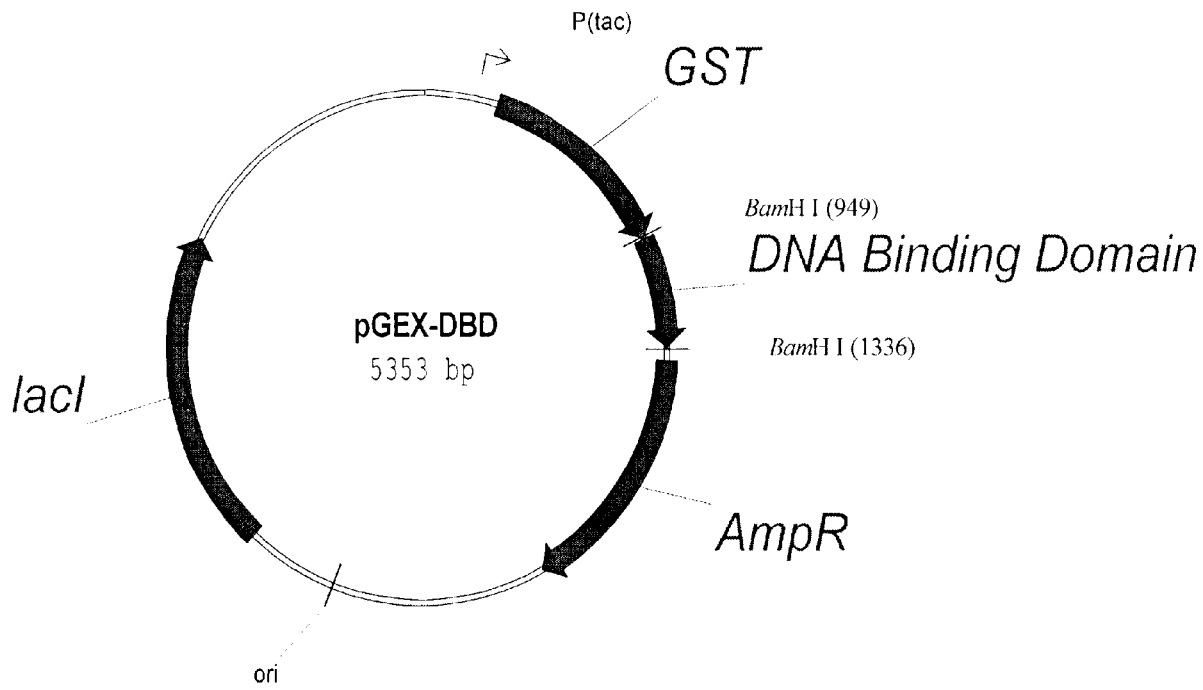
FIG. 6 is a map over the expression plasmid pGEX-DBD used for expression of the GST fusion protein GST/AfxDBD, GST/FKHRDBD, and GST/FKHRL1DBD.

DNA binding domain sequences of the human transcription factors Afx, FKHR, and FKHRL1 comprising amino acid residues G86 to A211 (hAfxDBD); L145 to A270 (hFKHRDBD); and G142 to A267 (hFKHRL1DBD) respectively (FIG. 1), were amplified by PCR using primers which included 5' and 3' BamHI sites, digested with BamHI and inserted into BamHI digested pGEX-2T-KB (FIG. 6). This vector originated from pGEX-2T (Amersham Pharmacia Biotech) after the introduction of a polylinker (5'GATCTGGTACCGAGCTCGGATCCCCGGG (SEQ ID NO:24), Scandinavian Gene Synthesis, Sweden) at the BamH1 and EcoR1 sites. The cloning cassette of the resulting pGEX-2T-KB vector contains, in addition to BamH1, EcoR1 and SmaI sites present in pGEX-2T, a KpnI, SacI and AvaI new restriction sites. The DNA binding domains were cloned in frame with the GST-tag in pGEX-2T-KB to produce pGEX-AfxDBD, pGEX-FKHRDBD, and pGEX-FKHRL1DBD. The sequences of the inserted DNA fragments were confirmed by DNA sequencing. Nucleotide sequences of primers used for the PCR amplification were (Scandinavian Gene Synthesis, Sweden):

AfxDBD5', 5'GACGACGGATCCGGGGCTGTAACAG-GTCCTC (SEQ ID NO:25);

AfixDBD3', 5'GACGACGGATCCTCAGGCTTTACT-GCGGCCCCG (SEQ ID NO:26);

FKHRDBD5', 5'GACGACGGATC-CCTCGCGGGGCAGCCGCGC (SEQ ID NO:27);

FKHRDBD3', 5'GACGACGGATCCTCAAGCTCGGCT-TCGGCTC (SEQ ID NO:28);

FKHRL1DBD5', 5'GACGACGGATCCGGGGCTC-CGGGCAGCCG (SEQ ID NO:29);

FKHRL1DBD3', 5'GACGACGGATCCTCATGCGCGGC-CACGGCTCTTG (SEQ ID NO:30).

```
AfxDBD5',    5'GACGACGGATCCGGGGCTGTAACAGGTCCTC      (SEQ ID NO:25);

AfxDBD3',    5'GACGACGGATCCTCAGGCTTTACTGCGGCCCCG   (SEQ ID NO;26);

FKHRDBD5',   5'GACGACGGATCCCTCGCGGGGCAGCCGCGC     (SEQ ID NO:27);

FKHRDBD3',   5'GACGACGGATCCTCAAGCTCGGCTTCGGCTC    (SEQ ID NO:28);

FKHRL1DBD5', 5'GACGACGGATCCGGGGGCTCCGGGCAGCCG    (SEQ ID NO:29);

FKHRL1DBD3', 5'GACGACGGATCCTCATGCGCGGCCACGGCTCTTG (SEQ ID NO:30).
```

II. Expression and Analysis of Recombinant Proteins

*Escherichia coli* BL21(DE3) (Novagen) were tansformed with pGEX-AfxDBD, pGEX-FKHRDBD, pGEXFKHRL1DBD, and pGEX-2T-KB (control), and transformants were used for inoculation of 20 ml of Luria broth medium (Luria, S. E., and Burrows, J. W. (1957), *J. Bacteriol.* 74: p. 461–476) containing 100 µg/ml carbenicillin (Sigma) and incubated in shaking flasks at 37° C. overnight. The cultures were diluted into 100 ml of fresh medium to an OD600 of 0.1 and incubated with vigorous shaking at 37° C. Expression was induced by addition of IPTG (final concentration 1 mM) at an OD600 of 0.5–0.6, and the incubation was continued for 2.5 h. Bacteria were harvested by centrifugation at 4,000×g for 15 min at 4° C. and the cell pellets were stored at −70° C.

Expression was analysed by SDS-polyacrylamide gel electrophoresis followed by staining with Coomassie brilliant blue (Sigma). Aliquots collected before and after IPTG induction were centrifuged at 20,000×g for 10 minutes. Pellets were resuspended in sample buffer containing DTT, and heated at 95° C. for 5 minutes. The samples were loaded on NuPAGE 10% Bis-Tris gels (Novex). Gels were run for 50 minutes at 200 volts in MOPS buffer (Biorad Model 100/500, Power Supply).

III. Preparation and Analysis of Bacterial Extracts

Cell pellets from 50 ml culture were thawed on ice before suspension in 2.5 ml TNT buffer (10 mM Tris-HCl, pH 8.0, 1 mM EDTA, 100 mM NaCl, 1% Triton X-100). Bacteria were lysed by addition of 2.5 mg lysozyme (Merck), incubation at 4° C. for 1 h, and sonication with vibra cell high intensity ultrasonic processor (Sonics & Materials) (4×20 s, 50% duty cycle, 3.5 output control). The lysates were cleared by ultracentrifugation at 100,000×g for 1 h at 7° C. DTT and glycerol were added to 2 mM and 15% final concentration, respectively, and the lysates were frozen in 1 ml aliquots at −70° C.

Aliquots of the bacterial extracts collected before and after the ultracentrifugation were analysed by SDS-polyacrylamide gel electrophoresis, as described above, followed by Coomassie brilliant blue staining, and Western blotting analysis. Proteins were transferred onto a 0.45 $\mu$m nitrocellulose membrane (Hybond, ECL, Amersham Pharmacia Biotech) for one hour at 100 volts by using a Novex Western Transfer Apparatus. The membrane was incubated in blocking buffer containing 5% low fat dried milk and 0.1% Tween20 in 1×PBS for 1 h to block nonspecific binding. Before addition of the primary antibody, the membrane was washed 2×5 minutes in washing buffer containing 1×PBS and 0.1% Tween20. Primary antibodies raised against the GST-tag (goat anti-GST antibody, Amersham Pharmacia Biotech) were used at a concentration of 5 $\mu$g/ml. The membrane was washed 3×10 minutes with washing buffer before addition of the secondary antibody (rabbit anti-goat antibody, from DAKO). Secondary antibodies were used at a concentration of 0.23 $\mu$g/ml. Incubation with primary and secondary antibodies was for one hour at room temperature. Before detection with the ECL-kit (Amersham Pharmacia Biotech), the membrane was washed 4×10 minutes in washing buffer. Equal volumes of detection solution 1 and 2 from the kit were added to the membrane and incubated for one minute. The membrane was placed in a film cassette and Hyperfilm-ECL (Amersham Pharmacia Biotech) was placed on top of the membrane for 3 s. The film was developed in a Curix 60 Agfa.

EXAMPLES

The invention will now be described in more detail by way of the following examples, which however should not in any way be construed as limiting the invention.

Example 1

I. Generation of Randomized Oligonucleotides

Sequence of the random oligonucleotide and primers (Scandinavian Gene Synthesis) used for DNA binding site selection procedure and sequencing:

N25: 5'CGCTCGAGGGATCCGAATTC(N)25TCTAGAAAGCTTGTCGACGC (SEQ ID NO:31);

N255'primer: 5'CGCTCGAGGGATCCGAATTC (SEQ ID NO:32);

N253'primer: 5'GCGTCGACAAGCTTTCTAGA (SEQ ID NO:33).

To obtain double-stranded oligonucleotides with randomized sequence in the central 25 base pairs as starting material for the selection procedure, 12 $\mu$g of N25 was mixed with 10 $\mu$g of N253'primer in 100 $\mu$l of 10 mM Tris-Cl, pH 7.5, 10 mM MgCl2, 1 mM DTT. The solution was heated to 95° C., followed by slow cooling in a water bath to 55° C., and kept at this temperature for 30 minutes. Following annealing at 55° C., the tube was transferred to 37° C., 10 $\mu$l of 10 mM dNTP (10 mM) and 2.5 $\mu$l Klenow enzyme (Boehringer, 2 U/$\mu$l) were added, and the incubation was continued at 37° C. for 30 minutes. NaCl was added to a final concentration of 0.25 M, and the DNA was precipitated with 300 $\mu$l ethanol at −20° C. overnight. The precipitated DNA was recovered by centrifugation, washed with 70% ethanol, recovered by centrifugation, vacuum dried, and finally resuspended in 148 $\mu$l dH20. Successful conversion of N25 to double-stranded oligonucleotides was verified by running an aliquot on a 4% NuSieve agarose gel (FMC, BioProducts).

II. Selection of Binding Sites

148 $\mu$l of double-stranded 65-mer was mixed with 10 $\mu$l of 2 mg/ml poly(dI-dC)/poly(dI-dC) (Amersham Pharmacia Biotech) and 40 $\mu$l of 5×binding buffer (1×binding buffer is 20 mM Hepes, pH 7.9, 50 mM KCl, 2 mM MgCl2, 0.5 mM EDTA, 10% glycerol, 0.1 mg/ml BSA, 2 mM DTT, 0.5 mM PMSF). This solution was divided into two eppendorf tubes and 1 $\mu$l of undiluted and 1/10-diluted bacterial extract, was added to each tube, respectively. The bacterial extract was estimated to contain approximately 500 ng fusion protein (SDS-PAGE analysis). This was done for GST/AfxDBD, GST/FKHRDBD, GST/FKHRL1DBD, and GST (control). Following incubation of the binding reactions at room temperature for 10 minutes, 50 $\mu$l of a 10% slurry of glutathione-Sepharose in 1×binding buffer (Amersham Pharmacia Biotech) were added and the tubes were flicked gently for 2 minutes to prevent the Sepharose from settling. The glutathione-Sepharose beads with bound protein-DNA complexes were pelleted in a microcentrifuge at 3,000×g for 1 minute. The supernatants were removed and the pellets were resuspended in 1 ml of ice-cold 1×binding buffer, transferred to new tubes, centrifuged, and the supernatants were removed. Three more 1 ml washes were made with the samples transferred to new tubes before the last centrifugation.

The washed glutathione-Sepharose pellets were resuspended in 50 $\mu$l of PCR buffer (10 mM Tris-Cl, pH 8.3, 50 mM KCl, 1.5 mM MgCl2, 0.001% gelatin) and transferred to 0.5-ml microcentrifuge tubes. Fifty microliters amplification mix (PCR buffer containing 0.4 mM dNTP, 2 $\mu$M N255'primer, and 2 $\mu$M N253'primer) and 0.5 $\mu$l Taq polymerase (Boehringer, 5 U/$\mu$l) were added and the samples were PCR amplified for 30 cycles (Perkin Elmer, Gene Amp PCR System 2400). Each cycle consisted of a 1 min incubation at 96° C. and a 30 s incubation at 60° C. The final amplification step consisted of a single 30 s incubation at 72° C. A 10 $\mu$ls aliquot of each selection was analysed on a 4% NuSieve agarose gel to verify the presence of a 65-bp product, and the rest of the PCR reaction was precipitated with 10 $\mu$l 5 M NaCl and 250 $\mu$l ethanol at −20° C. overnight. The precipitated 65-mer PCR products were recovered by centrifugation, washed with 70% ethanol, recovered by centrifugation, vacuum dried, and finally resuspended in 120

μl dH2O. The solutions were filtered through 0.45 μm Spin-x filters (Costar) to remove the Sepharose beads.

The second round of selection was identical to the first, except for the following modifications: The binding reaction was set up with 10μ of the Spin-x filtrate from the first amplification, 64 μl dH2O, 5 μl poly(dI-dC)(poly(dI-dC) (2mg/ml), 20 μl of 5×binding buffer and 1 μl of bacterial extract as described above for the first round of selection. After the last wash, the Sepharose pellets were resuspended in 100 μl PCR buffer and boiled. Fifty microliters were combined with 50 μl amplification mix. The remaining 50 μl were set aside as backup in case the PCR had to be repeated. The number of cycles in the PCR reaction was decreased to 20.

The following rounds of selection and amplification were identical to the second round, except that the number of cycles in the PCR reaction were decreased, from 30 cycles in the first amplification to 10 cycles in the sixth and last amplification, as the fraction of high-affinity binding sites in the DNA pool increased.

After the sixth round of selection and amplification, the PCR products were separated on a 4% NuSieve agarose gel, and purified using the QIAEX II Gel Extraction Kit (QIAGEN). A 10 μl aliquot of the purified PCR products was analysed on a 4% NuSieve agarose gel.

III. Cloning and Sequencing of Selected Oligonucleotides

The gel purified PCR products from the last selection and amplification cycle were cloned into the pCR-script SK(+) vector (1) (Stratagene) or the pT7Blue vector (2) (Novagen). E. coli XL1 Blue Ultra Competent cells (Stratagene) and NovaBlue competent cells (Novagen) were transformed with the ligation reactions from 1 and 2 respectively, followed by spreading of the transformation mixtures on Luria Agar (LA) plates containing 100 μg/ml of ampicillin, 80 μM IPTG, and X-gal. For each GST-fusion protein, 20 to 30 white colonies were selected, plasmid-DNA (70 μg/ml) prepared (QUIAGEN, Quiaprep spin), and digested with PvuII (Boeringer Mannheim) followed by analysis on a 4% NuSieve agarose gel. The clones were analysed by DNA sequencing and the central 25 bp of the insert were aligned using Vector NTI Suite, Multiple Sequence Alignment (Informax, USA).

Example 2

Production of GST Fusion Proteins

The DNA binding domains (DBD) of Afx, FKHR, and FKHRL1, were expressed as GST-fusion proteins. For this, the DBDs of the fork head proteins were inserted into the BamHI site of the pGEX-2T-KB plasmid, to produce pGEX-DBD plasmids. The sequence of the inserted DNA fragments were confirmed by DNA sequencing, except for the C-terminal of FKHRL1DBD. This part was GC-rich, which made it difficult to sequence. Even after several attempts with different sequence analysis the last 15 nucleotides could not be determined. However, even though the C-terminal was not confirmed the plasmid construct was used in following experiments. The GST-fusion proteins and GST alone (control) (see FIG. 1) were expressed in E.coli. A SDS polyacrylamide gel electrophoresis analysis of the expression before and after IPTG induction shows expression of GST-fusion proteins of expected sizes.

The nucleotide sequence encoding the fusion protein GST-Afx-DBD is shown in FIG. 7, and the corresponding amino acid sequence is shown in FIG. 8.

Insolubility of recombinant proteins can occur when expressing them in E. coli. The fusion proteins used here had different solubility properties, GST/FKHRDBD, GST/FKHRL1DBD, and GST were soluble, whilst GST-AfxDBD partly existed as inclusion bodies. However, there was still enough GST/AfxDBD in the soluble fraction to successfully complete the selection procedure.

Example 3

Generation of Randomized Oligonucleotide

To obtain the randomized oligonucleotides used as starting material in the selection of the DNA binding sites, single-stranded oligonucleotides with randomized sequences in the central 25 bases were converted to double-stranded oligonucleotide. The smear of bands observed in agarose gel underneath the 65-mer band presumably reflects partially converted double-stranded oligonucleotides.

I. Selection of DNA-binding Sites

Selection of DNA-binding sites for the fork head proteins, AFX, FKHR, and FKHRL1, was performed according to Pierrou et al. (S. Pierrou et al. (1995); Analytical biochemistry, 229, pp. 99–105), shown in FIG. 2. Binding reactions are set up with bacterial extract containing the GST-fusion protein, and double-stranded oligonucleotides for which the central 25 bp have been randomized. To minimize non-specific protein-DNA interactions, binding is done in the presence of high levels of poly(dI-dC)(poly(dI-dC). The GST fusion protein DNA-bound complex is recovered by the addition of glutathione-Sepharose beads. Following extensive washing of the resin, the bound oligonucleotides are rescued by polymerase chain reaction amplification. The amplified material is used as DNA-pool in the next cycle of selection and amplification. After six cycles the amplified oligonucleotides are cloned and DNA sequence determined.

The PCR products from each cycle of selection and amplification were analysed by agarose gel electrophoresis. For all of the GST-fusion proteins the gel shows a distinct band of 65 bp. The analysis of the PCR products for the GST-fusion proteins gave similar results after each round of selection. When GST alone (control) is used in the selection procedure, PCR products were found only after the first two rounds of selection, but not after subsequent cycles. This verifies that the oligonucleotides are selected by the fork head DBD moiety of the fusion proteins. Two different concentrations of bacterial extract were used for each fusion protein in the selection and amplification procedure. However the two different concentrations used in these experiments did not show any difference in terms of the amount of amplified oligonucleotides.

After the sixth round of selection and amplification, the PCR products selected by the various fork head fusion proteins were cloned, and 20–30 colonies from each selection were sequenced. The central 25 bp of the oligonucleotide sequences were aligned and the results for the Afx selection are shown in FIG. 3. A common motif can easily be identified for each fork head protein. The consensus alignment sequence obtained for the Afx transcription factor has a palindrome structure, AACATGTT (FIG. 3). The other two fork head proteins, FKHR and FKHRL1, share the DNA-binding sequence, GTAAA(C/T)A.

Figure 4:
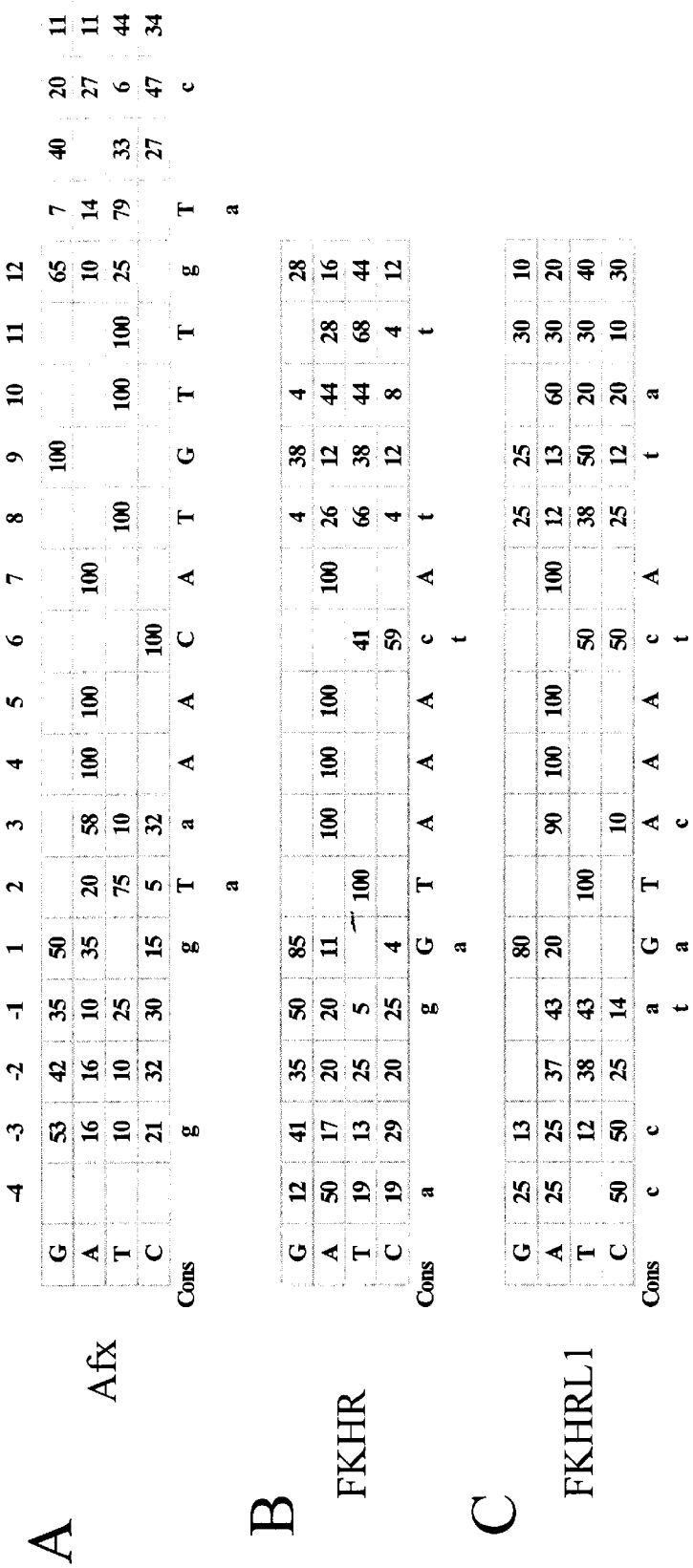
FIGS. 4a, 4b, and 4c are a summary of selected DNA binding sites for the three fork head proteins Afx, FKHR and FKHRL1. Numbers represent the frequency in percentage for each nucleotide at each position. The number of sequences on which this summary is based is 20, 27 and 10 for Afx, FKHR and FKHRL1, respectively.

The frequency of the four nucleotides in each position of the binding site was calculated from the aligned sequences (FIG. 4). To make sure that the calculation was based only on high-affinity sites, any sequences in which there were more than one possible match to the consensus motif were excluded. This ensured that oligonucleotides which produced sufficient binding energy to survive the selection procedure through the combined action of several, suboptimal binding sites, rather than a single, high-affinity site did not contribute to the final consensus.

Example 4

In order to produce a weight matrix representing a group of binding sites for a transcription factor, it is necessary to identify a representative frequency matrix. It is necessary to identify near-optimal alignments for each set of sites sequence displayed in FIGS. 4A, 4B and 4C. Most alignment methods are not designed for the small transcription factor binding sites with highly variable columns present between conserved positions. The Gibbs sampling expectation-maximumization method originally described by C. E. Lawrence et al. (1993); *Science,* 262 (5131), pp. 208–214, .J. W. Fickett (1996); *Mol. Cell Biol.,* 16 (1), pp. 43 7–44, has been utilized with modifications for DNA sequences introduced by J W Fickett, *Mol Cell Biol.* January 1996; 16(1):437–41.

This method determines patterns present in biopolymer sequences which are significantly stronger (more information content in terms of information theory) than random patterns. The program used performs 5 separate searches and reports back the strongest pattern detected. In the case of the Afx data, all 5 searches produced the same pattern. The user must specify the number of instances of the pattern expected, which impacts the output of the program.

Afx-specific Notes

For the Afx weight matrix, the sequences described in FIGS. 3 and 4A are utilized to find 24 sites or pattern instances of width 12 bp. The resulting frequency matrix is as shown in FIG. 5A. After conversion to a weight matrix and the knowledge adaptation procedure, the pattern is as shown in FIG. 5B. Suggested threshold score for sites to consider is 14.0, which is achieved 267 times in 22.2 megabases (22.000.000 basepairs) of genomic sequence.

FKHR-specific Notes

For the FKHR weight matrix, the sequences described in FIG. 4B are utilized to find 35 sites or pattern instances of width 8 bp. After conversion to a weight matrix and the knowledge adaptation procedure, the pattern obtained suggested that threshold score for sites to consider is 12.0, which is achieved 3284 times in 22.2 megabases (22.000.000 basepairs) of genomic sequence.

FKHRL1-specific Notes

For the FKHRL1 weight matrix, the sequences described in FIG. 4C are utilized to find 16 sites or pattern instances of width 7 bp. After conversion to a weight matrix and the knowledge adaptation procedure, the pattern obtained suggested that threshold score for sites to consider is 9.0, which is achieved 7487 times in 22.2 megabases (22.000.000 basepairs) of genomic sequence.

Searching for Potential Afx Sites

In order to screen the available genomic sequences for potential Afx sites, the model described above is used, and the range of scores for the sites obtained in the site selection assay is determined. A threshold score of 14.0 is used. The EMBL/GenBank database of sequences for entries with sequences scoring above this threshold was used for screening. By scoring is meant: For any given sequence as wide as the model, take the corresponding numbers for the observed nucleotide at each position and sum the numbers.

This search produced a number of hits. In order to create a subset of the sites for expert review, the list was narrowed to:

(1) genomic sequences present in a collection of genes selectively expressed in the liver or in adipocytes; and (2) GenBank entries which contained in the title line "promoter" or "enhancer" or "regulatory".

After expert curation, this list was narrowed to Table 1 below.

TABLE 1

Selected genomic gene sequences for potential Afx sites from transcripts expressed in liver/adipocytes and the EMBL-990629 sequence release

| Score | Clone/gene |
|---|---|
| 5.44 | Mouse M20497 adipose fatty acid binding protein |
| 5.75 | hPPARg2 promoter AB005520 |
| 7.5 | hPCK1 U31519 |
| 14.0 | hPAC-RPCI4-79 |
| 14.2 | mouse LPL (exon1) |
| | hChr17-HCIT104N19 |
| | proenkephalin U09941.1 |
| 15.3 | hChr20718J7 |
| | hOB-gene/exon3 |
| 15.4 | hBACRG118E13 |
| | mouse AC00529 |
| 15.5 | hNH0576I16 |
| | hAldolase reductase |
| 15.7 | hα-fetoprotein |
| 15.9 | hTyrosine amino transferase |
| 16.0 | HIV type-1 enhancer binding protein-2 |
| 16.4 | hApolipoprotein B-100, and hCOX-2 |
| 16.4 | hBacRG118E13 (NPY) |
| 16.5 | hPacCh14-rpCI4-794B2 |
| 18.0 | h c-fos |
| 18.2 | rat CYP4A1 |

This study has identified a novel DNA binding site for the human fork head transcription factor Afx from random sequence oligonucleotides. In FIG. 3 a set of sequences are aligned that have been selected using the GST-AfxDBD protein. A common motif can easily be identified comprising the nucleotide sequence AACATGTT.

Several studies of DNA target sites for other fork head proteins have been performed. All these studies have a seven base pair recognition core motif, (G/A)(T/C)(C/A)AA(C/T) A, in common, whereas sequences flanking either side do not share any obvious similarities (E Kaufmann et al. (1996); *Mechanisms of Development,* 57, pp. 3–20). The positions within the binding sites will be referred to relative to the first position of this core, i.e. the (G/A) position. The three adenosines at positions +4, +5, and +7, appear to be critical since they are conserved in all of the earlier studies and also in the selected response element sequences for the three fork head proteins Afx, FKHR, and FKHRL1. During the last years, different insulin response elements (IRE) have been published (R. M. O'Brien, et al. (1996). *Gene regulation in Diabetes Mellitus* Lippincott-Raven publishers, Philadelphia. pp. 234–242; G. J. P Kops, et al. (1999). *Nature,* 398, pp. 630–634; S. Guo et al (1999). *J. Biol. Chem.* 274, 17184–17192; J. E. Ayala et al. (1999). *Diabetes,* 48, 1885–1889; and S. K. Durham et al. (1999). *Endocrinology,* 140, 3140–3146). One of them is an element that has been identified in the promoter region of several genes repressed by insulin in a P13K/Akt-dependent manner, such as insulin-like growth factor binding protein-1 (IGFBP-1). This proposed IRE consists of 8 bp, (CAAAAC/TAA). A comparison of this core sequence with the selected consensus sequences for Afx, FKHR, and FKHRL1 reveals that the three adenosines are conserved also in this IRE.

The selected DNA binding site for Afx differs from the other two fork head proteins. The core sequence appears to be more specific than those for FKHR and FKHRL1, which show more variety among the clones, and it has a palindrome structure that is not observed for the other fork head proteins.

The novel response element according to the present invention, is useful in the screening for genes as diabetes drug targets, and also for the bioinformatic analysis of the human genome (See Example 4), providing a subset of genes transcriptionally responsive to insulin and also in construction and development of assays that enables and facilitates the analysis of genes interacting with the insulin receptor signaling pathway. Genes found in this screening can in turn then be used in other screening methods for compounds modifying the insulin receptor signaling pathway.

Flanking sequences have been shown to be important in contributing DNA-binding site specificity, while at the same time they are less well defined than the core. This has been shown more directly for some of the fork head proteins FREAC (S Pierrou et al. (1994) *EMBO J.*, 13, pp. 5002–5012).

What is claimed is:

1. An isolated nucleic acid sequence comprising an Afx response element, wherein the Afx response element comprises the nucleotide sequence AACATGTT, and wherein the Afx response element is contained in a promoter, intron, or intergenic sequence of the nucleic acid.

2. The nucleic acid sequence of claim 1, wherein the Afx response element is a cytokine response element.

3. The nucleic acid sequence of claim 1, wherein the Afx response element is an insulin response element.

4. A vector construct comprising the nucleic acid sequence of claim 1.

5. A host cell transformed with the vector construct of claim 4.

6. The vector of claim 4, wherein the Afx response element comprises the nucleotide sequence GTAAACAT-GTTGT (SEQ ID NO:34).

7. The vector of claim 4, wherein the Afx response element comprises the nucleotide sequence of any of SEQ ID NOs:1–20.

8. The vector of claim 4, wherein the Afx response element is operably linked to a nucleotide sequence encoding a protein, wherein the protein corresponds to the sequence of a naturally occurring polypeptide whose expression is regulated by insulin.

9. The vector of claim 4, wherein the Afx response element is operably linked to a nucleotide sequence encoding a reporter protein.

10. The nucleic acid sequence of claim 1, wherein the Afx response element comprises the nucleotide sequence GTAAACATGTTGT (SEQ ID NO:34).

11. The nucleic acid sequence of claim 1, wherein the Afx response element comprises the nucleotide sequence of any of SEQ ID NOs:1–20.

12. The nucleic acid sequence of claim 1, wherein the Afx response element is operably linked to a nucleotide sequence encoding a protein whose expression is regulated by insulin.

13. The nucleic acid sequence of claim 12, wherein the protein participates in the regulation of glucose transport.

14. The nucleic acid sequence of claim 1, wherein the Afx response element is operably linked to a nucleotide sequence encoding a reporter protein.

15. The nucleic acid sequence of claim 1, wherein the nucleic acid sequence consists of the nucleotide sequence AACATGTT.

* * * * *

SEQUENCE LISTING

<160> NUMBER OF SEQ ID NOS: 34

<210> SEQ ID NO 1
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 1
gccccactcc ataacatgtt gttc                                            24

<210> SEQ ID NO 2
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 2
ggccgcggat aacaacatgt tgttg                                           25

<210> SEQ ID NO 3
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 3
ggccgactat caacatgttt gcctg                                           25

<210> SEQ ID NO 4
<211> LENGTH: 25
<212> TYPE: DNA
<213> ORGANISM: Artificial Sequence
<220> FEATURE:
<223> OTHER INFORMATION: synthetically generated oligonucleotide
<221> NAME/KEY: misc_feature
<222> LOCATION: (1)...(25)
<223> OTHER INFORMATION: n = A,T,C or G

<400> SEQUENCE: 4
gnaaccgnct gttgtnaaca tgttg                                           25

<210> SEQ ID NO 5
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 5
ggacggtagg ggagtaaaca tgttg                                           25

```
<210> SEQ ID NO 6
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 6
ggcgggaggt gtcaacatgt tgtgc                                    25

<210> SEQ ID NO 7
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 7
ggcacccgca gtaaacatgt tatgc                                    25

<210> SEQ ID NO 8
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 8
ggcatagctc tgtgtaaaca tgttg                                    25

<210> SEQ ID NO 9
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 9
ggcaggacgg tacacaaaca tgttg                                    25

<210> SEQ ID NO 10
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 10
ggcatcaaca tgtttataat gggtg                                    25

<210> SEQ ID NO 11
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 11
ggcagcggta aacatgttgt ctccc                                    25

<210> SEQ ID NO 12
<211> LENGTH: 25
<212> TYPE: DNA
<213> ORGANISM: Artificial Sequence
<220> FEATURE:
<223> OTHER INFORMATION: synthetically generated oligonucleotide
```

```
<400> SEQUENCE: 12
ggcccacggt caacatgttt tgatg                                              25

<210> SEQ ID NO 13
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 13
ggcggggact cgggtaaaca tgttg                                              25

<210> SEQ ID NO 14
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 14
ggagcataaa catgttgttg gcggc                                              25

<210> SEQ ID NO 15
<211> LENGTH: 25
<212> TYPE: DNA
<213> ORGANISM: Artificial Sequence
<220> FEATURE:
<223> OTHER INFORMATION: synthetically generated oligonucleotide
<221> NAME/KEY: misc_feature
<222> LOCATION: (1)...(25)
<223> OTHER INFORMATION: n = A,T,C or G

<400> SEQUENCE: 15
ggcggtaaac atgttgngat cagng                                              25

<210> SEQ ID NO 16
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 16
gggcgggata aacatgttat gctcc                                              25

<210> SEQ ID NO 17
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 17
ggtaggcagc acaacatgtt taccc                                              25

<210> SEQ ID NO 18
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 18
ggtacatacg gtaaacatgt tgtgc                                              25
```

```
<210> SEQ ID NO 19
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 19
gggagcccca taacatgttt tcacg                                       25

<210> SEQ ID NO 20
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 20
gggcccaggc ataaacatgt tgttg                                       25

<210> SEQ ID NO 21
<211> LENGTH: 15
<212> TYPE: DNA
<213> ORGANISM: Artificial Sequence
<220> FEATURE:
<223> OTHER INFORMATION: consensus sequence

<400> SEQUENCE: 21
gggtaaacat gttgt                                                  15

<210> SEQ ID NO 22
<211> LENGTH: 1073
<212> TYPE: DNA
<213> ORGANISM: Artificial Sequence
<220> FEATURE:
<223> OTHER INFORMATION: synthetically generated GST-AfxDBD construct

<400> SEQUENCE: 22 atgtcccta  tactaggtta  ttggaaaatt  aagggccttg  tgcaacccac  tcgacttctt    60
ttggaatatc  ttgaagaaaa  atatgaagag  catttgtatg  agcgcgatga  aggtgataaa   120
tggcgaaaca  aaaagtttga  attgggtttg  gagtttccca  atcttcctta  ttatattgat   180
ggtgatgtta  aattaacaca  gtctatggcc  atcatacgtt  atatagctga  caagcacaac   240
atgttgggtg  gttgtccaaa  agagcgtgca  gagatttcaa  tgcttgaagg  agcggttttg   300
gatattagat  acgtgttttc  gagaattgca  tatagtaaag  actttgaaac  tctcaaagtt   360
gattttctta  gcaagctacc  tgaaatgctg  aaaatgttcg  aagatcgttt  atgtcataaa   420
acatatttaa  atggtgatca  tgtaacccat  cctgacttca  tgttgtatga  cgctcttgat   480
gttgttttat  acatggaccc  aatgtgcctg  gatgcgttcc  caaaattagt  ttgttttaaa   540
aaacgtattg  aagctatccc  acaaattgat  aagtacttga  atccagcaa  gtatatagca   600 tggccttttgc  agggctggca  agccacgttt  ggtggtggcg  accatcctcc  aaaatcggat   660
ctggttccgc  gtggatctgg  taccgagctc  ggatccgggg  ctgtaacagg  tcctcggaag   720
ggaggctccc  gccggaatgc  ctggggaaat  cagtcatatg  cagaactcat  cagccaggcc   780
attgaaagcg  ccccggagaa  gcgactgaca  cttgcccaga  tctacgagtg  gatggtccgt   840
actgtaccct  acttcaagga  caagggtgac  agcaacagct  cagcaggatg  gaagaactcg   900
atccgccaca  acctgtccct  gcacagcaag  ttcatcaagg  ttcacaacga  ggccaccggc   960
```

```
aaaagctctt ggtggatgct gaaccctgag ggaggcaaga gcggcaaagc cccccgccgc  1020
cgggccgcct ccatggatag cagcagaagc tgctccgggg ccgcagtaaa gcc          1073
```

<210> SEQ ID NO 23
<211> LENGTH: 358
<212> TYPE: PRT
<213> ORGANISM: Artificial Sequence
<220> FEATURE:
<223> OTHER INFORMATION: synthetically generated GST-AfxDBD construct

<400> SEQUENCE: 23

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Gly Thr Glu Leu Gly Ser Gly Ala Val Thr Gly Pro Arg Lys
225                 230                 235                 240

Gly Gly Ser Arg Arg Asn Ala Trp Gly Asn Gln Ser Tyr Ala Glu Leu
                245                 250                 255

Ile Ser Gln Ala Ile Glu Ser Ala Pro Glu Lys Arg Leu Thr Leu Ala
            260                 265                 270

Gln Ile Tyr Glu Trp Met Val Arg Thr Val Pro Tyr Phe Lys Asp Lys
        275                 280                 285

Gly Asp Ser Asn Ser Ser Ala Gly Trp Lys Asn Ser Ile Arg His Asn
    290                 295                 300

Leu Ser Leu His Ser Lys Phe Ile Lys Val His Asn Glu Ala Thr Gly
305                 310                 315                 320

Lys Ser Ser Trp Trp Met Leu Asn Pro Glu Gly Gly Lys Ser Gly Lys
                325                 330                 335

Ala Pro Arg Arg Arg Ala Ala Ser Met Asp Ser Ser Ser Lys Leu Leu
            340                 345                 350
```

Arg Gly Arg Ser Lys Ala
          355

<210> SEQ ID NO 24
<211> LENGTH: 28
<212> TYPE: DNA
<213> ORGANISM: Artificial Sequence
<220> FEATURE:
<223> OTHER INFORMATION: polylinker sequence

<400> SEQUENCE: 24
gatctggtac cgagctcgga tccccggg                                      28

<210> SEQ ID NO 25
<211> LENGTH: 31
<212> TYPE: DNA
<213> ORGANISM: Artificial Sequence
<220> FEATURE:
<223> OTHER INFORMATION: primer for PCR

<400> SEQUENCE: 25
gacgacggat ccggggctgt aacaggtcct c                                  31

<210> SEQ ID NO 26
<211> LENGTH: 33
<212> TYPE: DNA
<213> ORGANISM: Artificial Sequence
<220> FEATURE:
<223> OTHER INFORMATION: primer for PCR

<400> SEQUENCE: 26
gacgacggat cctcaggctt tactgcggcc ccg                                33

<210> SEQ ID NO 27
<211> LENGTH: 30
<212> TYPE: DNA
<213> ORGANISM: Artificial Sequence
<220> FEATURE:
<223> OTHER INFORMATION: primer for PCR

<400> SEQUENCE: 27
gacgacggat ccctcgcggg gcagccgcgc                                    30

<210> SEQ ID NO 28
<211> LENGTH: 31
<212> TYPE: DNA
<213> ORGANISM: Artificial Sequence
<220> FEATURE:
<223> OTHER INFORMATION: primer for PCR

<400> SEQUENCE: 28
gacgacggat cctcaagctc ggcttcggct c                                  31

<210> SEQ ID NO 29
<211> LENGTH: 30
<212> TYPE: DNA
<213> ORGANISM: Artificial Sequence
<220> FEATURE:
<223> OTHER INFORMATION: primer for PCR

<400> SEQUENCE: 29
gacgacggat ccgggggctc cgggcagccg                                    30

<210> SEQ ID NO 30
<211> LENGTH: 34

```
<212> TYPE: DNA
<213> ORGANISM: Artificial Sequence
<220> FEATURE:
<223> OTHER INFORMATION: primer for PCR

<400> SEQUENCE: 30
gacgacggat cctcatgcgc ggccacggct cttg                    34

<210> SEQ ID NO 31
<211> LENGTH: 65
<212> TYPE: DNA
<213> ORGANISM: Artificial Sequence
<220> FEATURE:
<223> OTHER INFORMATION: oligonucleotide for DNA binding site selection
<221> NAME/KEY: misc_feature
<222> LOCATION: (1)...(65)
<223> OTHER INFORMATION: n = A,T,C or G

<400> SEQUENCE: 31
cgctcgaggg atccgaattc nnnnnnnnnn nnnnnnnnnn nnnnntctag aaagcttgtc    60
gacgc                                                                65

<210> SEQ ID NO 32
<211> LENGTH: 20
<212> TYPE: DNA
<213> ORGANISM: Artificial Sequence
<220> FEATURE:
<223> OTHER INFORMATION: primer for DNA binding site selection

<400> SEQUENCE: 32
cgctcgaggg atccgaattc                                    20

<210> SEQ ID NO 33
<211> LENGTH: 20
<212> TYPE: DNA
<213> ORGANISM: Artificial Sequence
<220> FEATURE:
<223> OTHER INFORMATION: primer for DNA binding site selection

<400> SEQUENCE: 33
gcgtcgacaa gctttctaga                                    20

<210> SEQ ID NO 34
<211> LENGTH: 13
<212> TYPE: DNA
<213> ORGANISM: Artificial Sequence
<220> FEATURE:
<223> OTHER INFORMATION: binding motif

<400> SEQUENCE: 34
gtaaacatgt tgt                                           13
```